United States Patent [19]

Herring et al.

[11] Patent Number: 5,747,268
[45] Date of Patent: May 5, 1998

[54] TUMOR MARKER CONTROL

[75] Inventors: Kathryn Herring, Miami; Denise Sandberg, Davie, both of Fla.

[73] Assignee: Dade International Inc., Deerfield, Ill.

[21] Appl. No.: 351,869

[22] Filed: Dec. 8, 1994

Related U.S. Application Data

[63] Continuation-in-part of Ser. No. 52,001, Apr. 22, 1993, abandoned.

[51] Int. Cl.$^6$ .......................... G01N 33/574; G01N 33/53
[52] U.S. Cl. .......................... 435/7.23; 436/64; 436/813; 435/967; 530/344
[58] Field of Search .................................. 435/7.23, 967; 436/64, 813; 530/344

[56] References Cited

U.S. PATENT DOCUMENTS 4,489,167  12/1984  Ochi et al. .............................. 436/518

FOREIGN PATENT DOCUMENTS

| | | |
|---|---|---|
| 040058A | 5/1981 | European Pat. Off. . |
| 351117A | 7/1989 | European Pat. Off. . |
| 9116632 | 10/1991 | WIPO . |
| 9208976 | 5/1992 | WIPO . |

OTHER PUBLICATIONS

Evaluation of Human Serum Based Tumor Marker Control. D. Chapman, L. Fontana. J. Nucl Med Allied Sci 1989; 33 (suppl to No. 3): 114–117.

Purification and Complete Amino acid Sequence of Novel B2–Microglobulin. H. Odani, R. Oyama, K. Titani, H. Ogawa, A. Saito. Biochemical and Biophysical Rsearch Comm. pp. 1223–1229. vol. 168, No. 3, 1990, May 16, 1990.

Chemical Studies of Tissue Polypeptide Antigen (TPA). II.* Partial Amino Acid Sequences of Cyanogen Bromide Fragments of TPA Subunit $B_1$. P. Redelius, B. Luning, B. Bjorklund. Aca Chemica Scandinavica B34 (1980) 265–273.

Mechanism of Clearance of Circulating CA19–9 in Rats. M. Adachi, T. Sekine, A. Umemoto, S. Tsukikawa, K. Imai, A. Yachi. Tumor Biol 1990: 11: 51–58.

A Simple and Rapid Method for the Isolation of Human Alpha–fetoprotein from Human Cord Serum. Institute of Radioecology and Applied Nuclear Techniques, Kosice, Czechoslovakia; Research Institute for Child Development, Charles University, 150 00 Prague, Czechoslovakia. Neoplasma, 34, 4, 1987 pp. 491–496.

Immunoadsorbent Purification of Carcinoembryonic Antigen using a Monoclonal Antibody: a Direct Comparison with a Conventional Method. C.H.J. Ford, F. Macdonald, J.A. Griffin, P. Life, S.E. Bartlett. Tumor Biol 1987; 8: 241–250.

Evaluation of Human Based Multi–Level Control for Cancer Antigen Testing. Kathryn Herring, Denise Sandberg and Julia Monticello. (Baxter Diagnostics Inc) Miami, FL 33174). Clin Chem. vol. 40, No. 6, 1994, p. 1012.

A New Specialty Control: Special–T Marker. Kathryn Herring. Diagsource, Nov. 1993, vol. 3, No. 2, pp. 1–2.

Reimer et al., "The U.S. National Reference Preparation for Alpha–Fetoprotein in Mid–Pregnancy Maternal Serum," Clinical Chemistry 28:709–716 (1982).

*Primary Examiner*—Toni R. Scheiner
*Attorney, Agent, or Firm*—Cynthia G. Tymeson

[57] ABSTRACT

The present invention provides a stable control serum or plasma for tumor diagnosis, wherein the control contains the tumor markers relevant for the diagnosis of tumors. The serum or plasma has a reduced lipid content. The present invention also provides for a method of making the control.

13 Claims, No Drawings

TUMOR MARKER CONTROL

This application is a continuation-in-part of U.S. Ser. No. 08/052,001 filed on Apr. 22, 1993, now abandoned.

FIELD OF THE INVENTION

This invention relates generally to the field of stable human serum based controls for use in in vitro diagnostic assays and more specifically to stable human serum based controls for use in monitoring the precision of in vitro diagnostic assays for tumor markers.

BACKGROUND OF THE INVENTION

Tumor markers are substances released by tumor cells into the blood stream. The tumor markers can be detected in serum or other body fluids and are useful for clinically monitoring various malignancies. The term tumor marker has been extended to include cell or tissue characteristics, such as oncogenes or abnormally expressed proteins such as enzymes, hormones, and receptors that are related to and assist in identifying the tumor type.

Clinical oncologists measure the presence and/or amount of these markers in bodily fluids to assist them in the diagnosis of the condition, as well as for prognosis and the monitoring of the treatment of the patient. Serum assays of tumor markers are commercially available. These serum assays are performed using assay systems such as radioimmunoassay, enzyme immunoassay, fluorescence immunoassays and other clinical analysis techniques.

Controlling and monitoring the accuracy, precision, and reliability of these assay systems is critical to ensure that the patient receives the correct treatment and that the results of the assays are medically relevant.

Currently, some human serum based controls are commercially available. Controls, generally, are in levels representing specific ranges, for example a high, low, and/or normal range. These commercially available tumor control products include Cancer Antigen Controls, from POLYMEDCO, T-MARKERS QUALITY CONTROL SERUM, from NMS Pharmaceuticals, Inc. and LYPHOCHEK® Tumor Marker Control, from BIO-RAD. Currently available commercial controls, however, lack many of the tumor markers that are required by the clinical oncologists. Moreover, the currently available commercial controls have limited clarity, limited lyophilized stability and limited reconstituted stability. Also, some of the commercially available controls are only two level controls (i.e. High and Low). In addition, the concentrations of some of the components in the commercially available controls are either too high or too low to be completely useful.

Although methods have been published to purify some of the tumor markers many of these methods are tedious and require several steps. Each additional step results in a lower yield of the tumor marker. Tumor markers, for use in the controls do not necessarily need the high degree of purity resulting from some of these purification schemes.

Thus, a need exists for a tumor marker control that has a wider variety of tumor markers, has discrete useful ranges of the markers and has an enhanced optical clarity and stability. A need also exists for simpler methods of purification of some of the tumor markers which result in a high yield and a purity sufficient for the intended use.

SUMMARY OF THE INVENTION

The human based serum or plasma control according to the present invention preferably contains many of the tumor markers that are utilized by clinical oncologists to diagnose patients. The human based serum or plasma control according to the present invention has enhanced lyophilized and reconstituted stability and has enhanced optical clarity after reconstitution.

DETAILED DESCRIPTION OF THE INVENTION

The human based serum or plasma control of the present invention comprises a base of male human plasma or serum that has been lipid stripped and tumor markers. The tumor markers may include Adenocorticotropic Hormone (ACTH), Aldosterone, Alphafetoprotein (AFP), beta-2-microglobulin (B2M), CA 15-3®, CA 125®, CA 19-9®, CA 19-9® (Registered Trademarks of Centocor Diagnostics, a division of Centocor Inc.), CA 549, Carcinoembryonic Antigen (CEA), Ferritin, Gastrin, human Chorionic Gonadotropin (hCG), beta hCG, Gamma Enolase (NSE), Prolactin, Prostatic Acid Phosphatase (PAP), Prostatic Specific Antigen (PSA), Tissue Polypeptide Antigen (TPA), Calcitonin and LD-1. A preservative system should also be included in the control. The preservative system should include a preservative that is stable both prior to lyophilization and after lyophilization.

A preservative system is necessary in order to ensure reconstituted stability of certain markers especially enzymes that are very sensitive to proteases that are produced by microorganisms. A combination of preservatives are added. The preferred preservative system is a combination of gentamicin sulfate, cycloheximide and Proclin 300 (Rohm and Haas). The Proclin 300 is not effective after lyophilization, however, it is useful in controlling microbial growth during the manufacturing process. The gentamicin sulfate and cycloheximide are used to control growth of microorganisms after reconstitution. Sodium azide is not used mainly due to the hazard of the explosive properties of the azide.

The stability of the lyophilized control should be at least about a year and preferably at least about three years. The reconstituted stability of the majority of the components should be at least about seven days and preferably at least about fourteen days.

The base of human serum or plasma should be substantially from all male donors in order to preserve the stability of the PSA marker. In the presence of substantially all male serum or plasma, the PSA is very stable. Female serum and plasma may contain antibodies to this enzyme marker. The antibodies would effectively eliminate the PSA from the control solution. If the antibodies are successfully removed or their effects eliminated from the female serum or plasma, the resulting serum or plasma could be utilized as the base material.

The content of the lipids in the human serum or plasma must be reduced. The lipid content may be reduced by treating the serum or plasma with fumed silica or dextran sulfate or other known processes. The process used to reduce the lipids must ensure that the content of cholesterol and triglycerides in the human serum or plasma is less than about 20 mg/dL each after processing. There are at least three reasons to reduce the lipid content.

First, the stability of added tumor markers which are easily denatured or oxidized is increased when the lipid content is reduced. This is because when the lipids break down, they form oxidation by-products that can interfere with the stability of some of the markers. Moreover, the breakdown of lipids results in turbid solutions.

Second, the lipid reduction aids in the reconstitution process. The lyophilized control reconstitutes immediately upon the addition of the liquid when the lipids are eliminated. The reconstitution time of the lyophilized control is delayed by between about 15 to 30 minutes if serum or plasma containing normal amounts of lipids are utilized.

Third, high levels of lipids can cause interference in measuring some of the tumor markers. Thus, reduction of the level of lipids leads to a more accurate assay result.

The serum or plasma that is utilized as the base for the control should be assayed for the tumor markers that will be added prior to the addition of those tumor markers.

Table I is a classification of the various types of tumor markers that are added to the base material. Table II lists the tumor markers and the types of cancers that are usually associated with that marker. Table III lists sources of several of the tumor markers.

The tumor markers that are added into the base material must be relatively pure—that is not cross contaminated with other markers or contaminated with interfering substances. It is best to use sources of tumor markers that are native human forms; however, it has been found that many of the human source tumors produce more than one marker. The addition of this raw source to the base material makes it difficult to formulate a control with an accurate amount of each tumor marker. In some instances, the tumor marker could end up being added in an amount that is too high to be useful for low or normal control levels. Thus, to avoid this problem many of the tumor markers must be purified to remove cross-contamination. In addition, the tumor markers that are to be added to the base material should be assayed to determine the presence of cross-contaminants and known interfering substances.

B2M may be purified from urine that has been collected from patients having renal failure. Particulates are removed and the urine is diafiltered into an appropriate buffer and concentrated. The B2M, a protein, has an approximate molecular weight of about 11,000 daltons; thus, it can be purified using size exclusion chromatography such as gel filtration chromatography. Preferred gel materials are Ultragel ACA 54 or its equivalents. The fractions containing the B2M are pooled and concentrated to preferably at least about 1 g/dL, then the outcome of the purification can be determined using such known methods as electrophoresis. In addition, the B2M is tested by commercially available immunoassay. The B2M is stable when stored either at about 2–8 C. or frozen at less than about −20 C. The resulting B2M may contain up to as much as about 70% of impurities of immunoglobulins without effecting the usefulness of the B2M.

CA 125 is a marker that is specific to ovarian cancer. This marker may be found in ascites fluid that is collected from patients with ovarian cancer. The ascites fluid contains two markers, CA 125 and TPA. The contamination level of the TPA is very high; thus, in order to add an accurate amount of each of CA 125 and TPA, the markers must be separated. Both of these markers are shed into the serum during tumor growth and due to the similarities of these markers the separation of them is difficult. It was discovered that TPA binds to a hydrophobic interaction chromatography media, Phenyl Sepharose (Pharmacia), in the presence of phosphate buffer at about a physiological pH. A phosphate buffer of about 50 mM phosphate at a pH of about 7.2 is preferred. The ascites fluid is applied onto a column of Phenyl Sepharose. The majority of the CA 125 does not bind to the Phenyl Sepharose and flows directly through the column and is collected. The column is then washed with the phosphate buffer to which has been added about 2.5M urea. This buffer elutes the remaining CA 125. The column is then washed with the phosphate buffer to which has been added about 6M urea. The TPA is eluted with this buffer and collected.

Normally, chromatography using Phenyl Sepharose requires a high salt concentration for binding to occur. However, surprisingly, the TPA binds without a high salt concentration. Thus, it is surprising that the separation occurs because the separation is not due to the hydrophobic interaction. The separated proteins are buffer exchanged to remove the urea and are concentrated to a protein level of preferably about greater than 1 g/dL. The separation of the proteins may be confirmed by assaying the separated proteins using commercially available immunoassay techniques.

CEA, CA 19-9 and TPA are often obtained from the same source; thus, they must be separated from each other. CEA is a large glycoprotein of about 200,000 daltons and is found at elevated levels in the serum of patients with colon cancer. CEA is an oncofetal antigen that is expressed during intrauterine life and disappears after birth. Oncofetal antigens reappear in situations of repair or neoplastic growth in the organs where they appeared during gestation. Elevated levels have also been found in patients with lung, gastric, breast and pancreatic cancers. CA 19-9 is a tumor mucin antigen. Tumor mucins are high molecular weight glycoprotein from about 200,000 daltons to 1000 kDA and contain from about 25% to 80% carbohydrate. As a tumor marker CA 19-9 is elevated in patients with pancreatic cancer and gastrointestinal cancer.

One source of CEA, CA 19-9 and TPA is a cell line identified as SW 1116. SW 1116 is a human cell line developed from a colorectal carcinoma. The cancer cells excrete the antigens into a cell growth media. The cell growth medium is collected and frozen as it is produced. The cell supernatant is thawed and concentrated about 20 times. The concentrated supernatant is buffer exchanged into buffers such as phosphate buffers at physiological pHs. The preferred buffer is 50 mM phosphate at about pH 7.2.

Although CEA, CA 19-9 and TPA are somewhat different, they are all glycoproteins and are very difficult to separate by typical chromatography methods. Precipatation methods using perchloric acid treatment to precipatate the CEA have been suggested, however the process results in a low yield of the purified markers.

Thus, a method was developed to purify the three markers. The concentrated, buffer exchanged supernatant is applied onto a Phenyl Sepharose column. As described for the CA-125 purification, the TPA binds to the chromatography media without the presence of high salt. The column is then washed with phosphate buffer and the eluant is collected in fractions. As determined by immunoassay, these fractions contain mostly CA 19-9, but selected fractions contain CEA.

The CEA/CA 19-9 fractions could be separated and further purified by affinity chromatography using processes known in the art. In one process disclosed in Ford, C. H. J., et al. *Immunoadsorbent Purification of Carcinoembryonic Antigen using A Monoclonal Antibody: A Direct Comparison with a Conventional Method*, Tumor Biol. Vol. 8: pages 241–250 (1987), a column is prepared which contains a media that has an antibody specific to CEA attached to the chromatography media. This column can strip out the CEA and the CA 19-9 will pass through the column. The CEA can be stripped from the column. However there are other sources of commercially available CEA; thus, it is not necessary to utilize this method.

Since the CEA is not required to be obtained from this method, it is preferred to combine the fractions from the Phenyl Sepharose column and then wash the Phenyl Sepharose column with a phosphate buffer, preferably 50 mM phosphate at pH 7.2, containing from about 2 to 3M urea to remove any additional CA 19-9. The eluant is collected. All of the fractions containing CA 19-9 and CA 19-9 with CEA are combined. The column is next eluted with the same buffer but also containing about 6M urea. The TPA is eluted and collected.

The CA 19-9/CEA containing pool is buffer exchanged to remove the urea and concentrated to at least about 1 g/dL.

The CA 19-9 in the concentrate by freezing the concentrate. Long term freezing of the CA 19-9 results in a loss of activity of the CEA, however the activity of the CA 19-9 is preserved. Thus, the entire purification process can be simplified. The length of freezing time can be determined by testing aliquots of the concentrate for the presence of CEA by immunoassay techniques. The approximate recovery can be up to 100%.

Alternatively, the fractions containing the CEA/CA 19-9 can be discarded. Then, only the fractions containing CA 19-9 are pooled and concentrated.

The TPA is also buffer exchanged and concentrated as described above. The recovery of the TPA can also be up to about 100%. Cross-contamination is determined using immunoassay techniques.

The CEA can be obtained as described above using the monoclonal antibody method or it may be obtained from other commercially available sources. The CEA should be tested for cross-contamination with immunoassay methods prior to use in a control. If contamination is detected, the CEA must be purified using one of the methods known in the art, preferably the affinity method described above.

NSE is obtained from fresh or freshly frozen human brain. Purified NSE may be obtained commercially. The preferred method for purification is accomplished by preparing a homogenate of the brain, centrifuging the homogenate and collecting the supernatant. Next the supernatant is pelleted using 40% ammonium sulfate. The pellet is resuspended in a 10 mM Tris-phosphate buffer and dialyzed against the buffer then concentrated. The concentrate is chromatographed on DE-52 and eluted with a 0.15M–0.35M NaCl gradient. The peak containing the NSE is dialyzed, lyophilized and fractionated on Sephadex G 150 or the like. Polybufferexchanger chromatofocussing is used to focus the NSE. The NSE is then eluted and finally fractionated on G-150 (Superfine).

Finally, AFP must be purified. AFP is an oncofetal antigen like CEA. AFP is a glycoprotein expressed in fetal liver and digestive tract. In adults elevated levels of this antigen in serum is associated with malignant hepatoma and in some cases of ovarian and testicular cancers. The best source of this antigen is human cord serum collected at the time of birth. This serum contains high levels of AFP (about 60,000 ng/mL) and contains only one contaminating tumor marker, Prolactin.

There are methods for purifying AFP described in the art. For instance, Chudy D. and Zizkovsky V., *A simple and rapid method for the isolation of human alpha-fetoprotein from human cord serum*, Neoplasma 34 (4) pp. 491 to 496 (1987) describes one such procedure. For purposes of this invention, the preferred method of isolation of the AFP from the Prolactin is accomplished using ion exchange chromatography.

Using a 20 mM Tris buffer at pH 8.5 the cord serum is applied onto a cation exchange resin. At this pH and buffer strength the AFP binds to the column but the majority of the Prolactin does not bind to the column. Thus, the serum is added to the column, and the Prolactin is washed through the column. The Prolactin can be collected. The AFP can then be eluted off of the column using about 0.2 to 0.3M sodium chloride with the buffer.

The isolated AFP is then concentrated to about 1 mg/mL. Recovery of the AFP in this manner can be about 100%. The AFP purified in this manner may contain large quantities of albumin. However, this contaminant is not a problem since the serum or plasma based material contains albumin. The purified AFP can be tested using immunoassay procedures.

The other tumor markers such as ACTH, aldosterone, hCG, beta-hCG, CA 15-3, CA 549, Calcitonin, Ferritin, Gastrin, PAP, PSA, Prolactin and LD-1 are available commercially from several sources. These other markers can be obtained purified or can be purified by procedures well known in the art. For each tumor marker, cross-contamination can be assessed by immunoassay techniques. The LD-1 is added as a component of LDH by determining the amount of LD-1 present in LDH.

The solutions for the controls are formulated by first assaying the plasma or serum and all the specific tumor markers that are used to spike the plasma or serum. Table IV shows the target values for each of the specific tumor marker at each of the three levels of controls that are prepared. Calculations are performed by subtracting the concentration of each marker in the serum or plasma from the mean targeted value in Table IV, then adding the appropriate amount of each marker to each of the three levels of controls.

The tumor markers are added to the serum or plasma according to the stability of each marker. Markers such as B2M, AFP, Prolactin, hCG, Beta-hCG, CA-15-3, CA-19-9, CA 549, CA 125, CEA, Ferritin, TPA, and LD-1 (added as LDH) may be added and adjusted within a few days of lyophilization as long as the temperature of the serum or plasma is controlled within about 2 to 10 C. If all the materials are kept at between about 2–10 C., the ACTH, Gastrin, gamma enolase, and calcitonin (markers which have short term liquid stability) may be added up to about six hours prior to lyophilization. Preferably these markers are added immediately prior to lyophilization and the additions and adjustments are done at low temperatures, that is 2–10 C.

Each of the three levels of liquid controls are lyophilized using standard methods. The bottles containing the lyophilized controls are sealed under vacuum and then stored at about 4 C. The controls are reconstituted with water or other appropriate liquids such as buffers.

For ACTH, lyophilization studies are required to determine the loss of ACTH activity during the lyophilization process. Immunoassay methods are used to determine the loss of activity due to the process. The results can be used to determine the prelyophilization level of ACTH that is necessary to recover a specific post lyophilization level of ACTH.

The stability of all of the markers in the lyophilized control was determined to be four weeks at a stressed temperature of 37 C. See, Table V. This is thought to correspond to about 3 years when stored at 2–8 C. A reconstituted stability of at least two weeks was found for all markers except NSE, ACTH, gastrin and calcitonin. See, Table VI. The NSE, ACTH, gastrin and calcitonin must be used shortly after reconstituting with liquid. It was also found that the reconstituted stability can be prolonged for 30 days for all analytes except NSE, gastrin and calcitonin by freezing aliquots of the reconstituted material at −20 C. See, Table VII. The stability of the gastrin and calcitonin can be prolonged for seven days by freezing aliquots of the reconstituted material at −20 C. See, Table VIII. The stability of the NSE can be extended for twenty four hours by freezing aliquots of the reconstituted material at −20 C. See, Table VIII.

The following Examples are given for the purpose of illustrating the present invention:

EXAMPLE 1

Purification of B2M

A urine concentrate was prepared by collecting urine from patients with renal failure. The urine was pooled and sodium azide at 0.02% was added as a preservative. The urine was filtered through a membrane of less than 0.3 microns to remove all particulates and microbes. The urine was then diafiltered against seven volumes of 50 mM Tris buffer, pH 8.0 and concentrated to a volume 100 times the original volume. For example, 100 liters was concentrated to 1 liter. The concentrated urine was adjusted to a total protein concentration of about 9.0 g/dL using the above buffer.

About fifty mLs of the urine concentrate was applied to an Ultragel ACA 54 column. The sample size is dependent upon the column size and is equivalent to 2.5% of the total volume of the media. The length of the column must be about 100 cm for effective separation of the proteins. Fractions containing the B2M were combined, pooled and concentrated to about 1 g/dL.

Purification has also been accomplished on Superdex 75 (Pharmacia). However, for this application, the purification on Ultragel ACA 54 is superior.

Purification of CA 19-9 and TPA

About a fifty mL sample of a supernatant from SW1116, a cell line (supernatant available from Whitaker), was concentrated to one half the original volume. The sample was buffer exchanged three times with about fifty mL of 50 mM potassium phosphate at about pH 7.2. The final volume of the sample was about 35 mL. About twenty mLs of the sample were applied to a Phenyl Sepharose column. The column was washed with the buffer and fractions were collected. The fractions were evaluated for CEA and CA 19-9 activity using an immunoassay. Fractions containing CEA were pooled and concentrated and fractions containing CA 19-9 were pooled and concentrated. A buffer containing about 50 mM phosphate at pH 7.2 with increasing amounts of urea was applied to the column. The TPA was eluted with urea at about 6M. The TPA containing fractions were pooled and concentrated then diafiltered to remove the 6M urea.

The CA 19-9 fractions undergo long term storage to remove the activity of any CEA that contaminates the CA 19-9.

EXAMPLE 2

Preparation of the Controls

Delipidated serum from males was filtered through the following sequences of filters: a prefilter, a 1.2 micron filter, a 0.8 micron filter, a 0.45 micron filter and a 0.22 micron filter. The filtered serum was refrigerated. Proclin 300 from Rohm and Haas was added at a concentration of 1 mL per liter of serum. The serum was divided into two pools of about 1.92 liters per pool—designated as Pool 1 and Pool 2.

The serum was assayed for amounts of ACTH, Aldosterone, B2M, hCG, beta-hCG, CA 15-3, CA 19-9, CA 125, CA 549, calcitonin, CEA, Ferritin, gastrin, NSE, PAP, PSA, Prolactin, TPA, and LD-1 using immunoassay techniques.

Each of the markers were obtained through purifications as described herein or were obtained commercially. The amount of each marker was determined. An amount of each marker necessary to reach the values given in Table IV, Level I ranges were added to Pool 1. An amount of each marker to reach the values given in Table IV, Level III ranges were added to Pool 2. The amounts of marker were assayed and any adjustments were made by either adding additional amounts of marker.

Three milliliters aliquots from Pool 1 (Level 1) were filled into vials that had been chilled in a freezer for about one hour and three milliliter aliquots from Pool 2 (Level 3) were filled into vials that had been chilled in a freezer for about one hour. The vials were lyophilized, sealed under a vacuum and stored at about 4 C.

EXAMPLE 3

Assay of Serum Based Tumor Marker Control

Vials of the controls prepared in Example 2 were reconstituted with three milliliters of distilled water and inverted gently to mix. The markers contained in the Level 1 and Level 3 controls were assayed using a variety of immunoassay methods. The results are presented in Table IX.

TABLE 1

| CLASSIFICATION OF TUMOR MARKERS | | |
|---|---|---|
| 1. | Oncofetal Antigens AFP, CEA | Produced during fetal development and low levels in adults. Tumors cause re-expression of these proteins. |
| 2. | Tumor associated antigens | CA 19-9, CA 549, CA 15-3 Mucins(carbohydrate rich glycoproteins) excreted by the tumor cells. High molecular weight > 200 kda and 25 to 85% carbohydrate. |
| 3. | Hormones | hCG, ACTH, Calcitonin, Prolactin, Aldosterone, Gastrin |
| 4. | Serum Proteins | beta2-microglobulin, ferritin |
| 5. | Enzymes | PAP, NSE, LD1 |

TABLE II

| TUMOR MARKER CONTROL CLINICAL MARKERS | |
|---|---|
| TUMOR MARKER | SITE(S) |
| Adenocortitropic Hormone (ACTH) | Lung |
| Alphafetoprotein (AFP) | Testicular, Liver |
| Aldosterone | Kidney |
| Beta 2 Microglobulin | Bone Marrow |
| Beta Human Chorionic Gonadotropin | Gynecological, testicular |
| CA 15-3/CA 549 | Breast |
| CA 19-9 | Pancreas, Colorectal, Stomach |
| CA 125 | Ovarian |
| Carcinoembryonic Antigen (CEA) | Colorectal, Breast, Lung, Stomach, Pancreas |
| Ferritin | Liver |
| Gamma Enolase | Lung, Brain |
| Gastrin | Pancreas |
| Human Chorionic Gonadotropin (hCG) | Testicular |
| Lactate Dehydrogenase Isoenzyme (LD-1) | Brain |
| Prolactin | Pituitary |
| Prostatis Acid Phosphatase (PAP) | Prostate |
| Prostate Specific Antigen (PSA) | Prostate |
| Tissue Polypeptide Antigen (TPA) | Bladder, Prostate, Gynecological, Lung |

TABLE III

| TUMOR MARKER CONTROL | |
|---|---|
| ANTIGENS | SOURCE |
| B2 Microglobulin | Renal failure urine |
| CA 15-3/CA 549 | Breast ascites, Pleurol fluid, Hybritech mouse tumor |
| CA 19-9 | SW1116 Supernate |
| CEA | SW1116 Supernate |
| TPA | SW1116 Supernate Ovarian cancer ascites Pleural fluids |
| CA 125 | Ovarian cancer ascites Pleural fluid - breast |
| Prolactin | Human cord serum |
| Alpha-fetoprotein | Cord serum |

TABLE IV

TYPICAL VALUES TUMOR MARKER CONTROL

| Constituent | Units | Level 1 Ranges | Level II Ranges | Level III Ranges |
|---|---|---|---|---|
| Adenocorticotropic Hormone | pg/mL | 35 (20–50) | 65 (50–80) | 400 (350–450) |
| Alpha-Fetoprotein | ng/mL | 10 (7–13) | 75 (65–85) | 250 (230–270) |
| Aldosterone | pg/dL | 50 (30–70) | 110 (95–125) | 700 (650–750) |
| B-2 Microglobulin | ng/L | 1.5 (1–2) | 3 (2.5–3.5) | 12 (10–14) |
| Beta Human Chorionic Gonadotropin | IU/L | 5 (1–9) | 20 (15–25) | 450 (440–460) |
| Human Chorionic Gonadotropin | IU/L | 5 (1–9) | 20 (15–25) | 450 (440–460) |
| CA 15-3 | U/mL | 45 (30–60) | 200 (150–250) | >240 |
| CA 19-9 | U/mL | 30 (20–40) | 100 (90–110) | 400 (380–420) |
| CA 125 | U/mL | 20 (10–30) | 40 (35–45) | 400 (350–450) |
| CA 549 | U/mL | 15 (10–20) | 40 (35–45) | 65 (60–70) |
| Thyrocalcitonin | pg/mL | 30 (20–40) | 110 (100–120) | 600 (550–650) |
| Carcinoembryonic Antigen | ng/mL | 4 (3–5) | 15 (10–20) | 30 (25–35) |
| Ferritin | ng/mL | 30 (25–35) | 100 (95–105) | 450 (440–460) |
| Gastrin | pg/mL | 60 (50–70) | 200 (190–210) | 400 (390–410) |
| LDH-1 | U/L | 150 (130–170) | 250 (240–260) | 350 (340–360) |
| Gamma Enolase | ng/mL | 50 (40–60) | 100 (90–110) | 150 (140–160) |
| Prostatic Acid Phosphatase | ng/mL | 3 (2–4) | 11 (10–12) | 25 (23–27) |
| Prostatic Specific Antigen | ng/mL | 3 (2–4) | 15 (13–17) | 35 (33–37) |
| Prolactin | ng/mL | 5 (3–7) | 20 (18–22) | 150 (140–160) |
| Tissue Polypeptide Antigen | U/L | 30 (25–35) | 100 (90–100) | 500 (490–510) |

TABLE V

ACCELERATED STABILITY STUDIES
Four weeks @ 37 C.

| Analyte | Level I fresh | Level I 37 C. | Level II fresh | Level II 37 C. |
|---|---|---|---|---|
| AFP | 10.2 | 10.3 | 293 | 293 |
| Aldos | 79 | 74 | 800 | 780 |
| B2M | 1.0 | 0.97 | 4.2 | 4.2 |
| Gastrin | 77 | 72 | 289 | 275 |
| Calcitonin | 38 | 35 | 270 | 275 |
| ACTH | 33 | 34 | 461 | 486 |
| Ferritin | 31 | 27 | 692 | 697 |
| PAP | 2.1 | 1.9 | 17 | 16 |
| Prolactin | 6.8 | 6.6 | 171 | 170 |
| PSA | 3.0 | 3.0 | 37 | 37 |
| TPA | 48 | 48 | 953 | 957 |
| CA549 | 8.9 | 8.6 | 27 | 30 |
| CA 15-3 | 41 | 41 | 262 | 245 |
| beta hCG | 2.7 | 2.8 | 475 | 446 |
| hCG | 2.7 | 2.7 | 460 | 439 |
| CA125 | 18 | 18 | 356 | 361 |
| CEA | 2.9 | 2.9 | 57 | 57 |
| NSE | 14 | 12 | 65 | 51 |
| LDH | 286 | 260 | 782 | 756 |

TABLE VI

RECONSTITUTED STABILITY STUDIES
Fourteen days @ 2–8 C.

| Analyte | Level I fresh | Level I 14 Days | Level II fresh | Level II 14 Days |
|---|---|---|---|---|
| AFP | 10.2 | 10.6 | 293 | 294 |
| ALDOS | 79 | 81 | 804 | 850 |
| B2M | 1.1 | 1.0 | 4.2 | 4.4 |
| CA 19-9 | 35 | 33 | 249 | 241 |
| Ferritin | 31 | 28 | 693 | 671 |
| PAP | 2.1 | 2.0 | 16.9 | 16.4 |
| Prolactin | 6.8 | 6.3 | 171 | 170 |
| PSA | 3.0 | 2.6 | 37 | 32 |
| TPA | 48 | 46 | 953 | 957 |
| CA549 | 8.9 | 8.9 | 27 | 30 |
| CA 15-3 | 41 | 43 | 165 | 158 |
| beta hCG | 2.7 | 2.6 | 475 | 446 |
| hCG | 2.7 | 2.7 | 422 | 414 |
| CA125 | 18 | 20 | 356 | 360 |
| CEA | 2.9 | 2.6 | 57 | 56 |
| LD1 | 47.7 | 49.8 | 51 | 51 |

TABLE VII

FROZEN STABILITY STUDIES
Thirty Days @ −20 C.

| Analyte | Level I 2–8 C. | Level I −20 C. | Level II 2–8 C. | Level II −20 C. |
|---|---|---|---|---|
| Aldos | 76 | 78 | 840 | 834 |
| AFP | 11 | 11 | 300 | 297 |
| B2M | 0.98 | 0.97 | 4.7 | 4.8 |
| ACTH | 15 | 17 | 408 | 418 |
| Ferritin | 31 | 28 | 726 | 686 |
| PAP | 2.2 | 2.1 | 20 | 20 |
| PSA | 2.6 | 2.6 | 33 | 33 |
| Prolactin | 4.2 | 4.4 | 125 | 133 |
| TPA | 56 | 54 | 779 | 854 |
| CA549 | 9.1 | 9.9 | 36 | 35 |
| CA 15-3 | 23 | 23 | 100 | 102 |
| beta hCG | 2.6 | 2.6 | 426 | 438 |
| CA125 | 25 | 25 | 448 | 474 |
| CEA | 2.6 | 2.6 | 60 | 61 |
| CA19-9 | 55 | 55 | 276 | 277 |
| LDH | 252 | 247 | 756 | 746 |
| LD-1 | 48% | 48% | 51% | 51% |

TABLE VIII

FROZEN STABILITY STUDIES

| Analyte | Level I 2-8 C. | Level I -20 C. | Level II 2-8 C. | Level II -20 C. |
|---|---|---|---|---|
| | Seven Days @ -20 C. | | | |
| Gastrin | 101 | 98 | 322 | 313 |
| Calcitonin | 123 | 110 | 342 | 353 |
| | Twenty Four Hours @ -20 C. | | | |
| NSE | 10 | 10 | 54 | 54 |

TABLE IX

INSTRUMENT/METHOD COMPARISON

| Analyte | Method | Units | Level 1 | Level 3 |
|---|---|---|---|---|
| ACTH | Diagnostic Products | pg/mL | 33 | 461 |
| | Incstar RIA | pg/mL | 14 | 466 |
| | Nichols Alegro RIA | pmol/L | 14 | 69 |
| | Clinical Assays | pg/mL | 20 | 466 |
| Aldosterone | Diagnostics Products | pg/mL | 79 | 875 |
| AFP | Clinical Assays | ng/mL | 2.9 | 263 |
| | Diagnostics Products | ng/mL | 5.9 | 238 |
| | Hybritech Stratus | ng/mL | 8.5 | 324 |
| | Hybritech Tandem E | ng/mL | 9.0 | 284 |
| | Amerlex-M AFP RIA | ng/mL | 10.5 | 286 |
| Beta-2-microglobulin | Abbott IMX | mg/L | 1.0 | 4.2 |
| | Pharmacia | mg/L | 1.1 | 4.4 |
| CA 15-3* | Byk Sangtec RIA | U/mL | 30 | 146 |
| | CIS ELSA | U/mL | 41 | 260 |
| | Sorin Gammadab | U/mL | 30 | 178 |
| CA 19-9* | Abbott IMX | U/mL | 45 | 344 |
| | Byk Sangtec RIA | U/mL | 26 | 171 |
| | Centocor ER | U/mL | 29 | 221 |
| | CIS ELSA | U/mL | 51 | 289 |
| CA 125* | Centocor | U/mL | 22 | 377 |
| CA 549 | Hytritech Tandem-R | U/mL | 10 | 30 |
| CEA | Abbott IMX | ng/mL | 4.9 | 108 |
| | Abbott RIA | ng/mL | 3.9 | 110 |
| | Hybritech Stratus | ng/mL | 2.7 | 56 |
| | Hybritech Tandem E | ng/mL | 2.4 | 60 |
| | Roche EIA | ng/mL | 3.5 | 94 |
| Ferritin | Abbott IMX | ng/mL | 23 | 760 |
| | Clinical Assays (GC) | ng/mL | 23 | 600 |
| | Clinical Assays (GD) | ng/mL | 23 | 548 |
| | Diagnostics Products | ng/mL | 25 | 623 |
| Gastrin | Clinical Assays | pg/mL | 172 | 460 |
| | Diagnostics Products | pg/mL | 56 | 347 |
| hCG | Abbott IMX | mIU/mL | 2.4 | 387 |
| | Clinical Assays | mIU/mL | 8.4 | 456 |
| | Diagnostics Products | mIU/mL | 2.9 | 385 |
| | Diagnostics Products (DA) | | 11 | 94 |
| | Stratus Immunoassay | mIU/mL | 5.0 | 460 |
| | Serono | mIU/mL | 4.2 | 434 |
| beta hCG | Abbott IMX | mIU/mL | 3.6 | 453 |
| | Hybritech Tandem-R | mIU/mL | 2.2 | 341 |
| | Stratus Immunoassay | mIU/mL | 2.8 | 433 |
| | Medgenix RIA 100 | ng/mL | 1.0 | 3.5 |
| Gamma Enolase | Byk-Sangtec | ug/L | 14 | 65 |
| Prolactin | CIS HPRLK-PR | mIU/L | 70 | 4546 |
| | CIS ELSA | ng/mL | 3.9 | 54 |
| | Clinical Assays | ng/mL | below range | 90 |
| | Diagnostics Products | ng/mL | 3.5 | 141 |
| | Hybritech Tandem-E | ng/mL | 7.1 | 152 |
| | Stratus Immunoassay | ng/mL | 4.0 | 152 |
| PAP | Clinical Assays | ng/mL | 1.1 | 16 |
| | Hybritech Tandem-E | ng/mL | 2.1 | 19 |
| | Hybritech Tandem-R | ng/mL | 2.6 | 24 |
| | Hybritech Stratus | ng/mL | 2.6 | 17 |
| PSA | Abbott IMX | ng/mL | 4.6 | 59 |
| | Hybritech Stratus | ng/mL | 8.1 | 106 |
| | Hybritech Tandem-R | ng/mL | 2.4 | 35 |
| TPA | Byk-Sangtec | ng/mL | 54 | 978 |
| Calcitonin | Diagnostic Products | pg/mL | 61 | 173 |
| | Incstar, II RIA | pg/mL | 129 | 367 |

*CA 15-3, Ca 19-9, CA 125 are trademarks of Centocor Diagnostics, a division of Centocor

We claim:

1. A control for the determination of tumor markers comprising a mixture of:

(a) a base material comprising human serum or plasma having reduced lipids;

(b) a plurality of tumor markers said tumor markers comprising at least PSA and ACTH wherein the PSA and ACTH in the control each have a reconstituted stability of at least thirty days at about -20 C.

2. The control of claim 1 wherein said control is lyophilized.

3. The control of claim 1 wherein the tumor markers are relatively pure.

4. A control for the determination of tumor markers comprising a mixture of:

(a) a base material comprising human serum or plasma having reduced lipids;

(b) a plurality of tumor markers said tumor markers comprising PSA and consisting of at one of the following additional tumor markers selected from gastrin, gamma enolase, CA 15-3, CA 549, and LD-1 wherein the PSA in the control has a reconstituted stability of at least thirty days at about -20 C.

5. A method to separate CA 125 from TPA comprising:

a) adding a fluid containing CA 125 and TPA to a hydrophobic interaction chromatography media in the presence of a phosphate buffer at about physiological pH; and b) collecting the eluant.

6. The method of claim 5 further comprising:

a) washing the chromatography media with said buffer wherein said buffer also contains between at least about 2.5M urea to less than about 6M urea; and b) collecting the eluant.

7. The method of claim 6 further comprising:

a) washing the chromatography media with at least about 6M urea; and b) collecting the eluant.

8. The method of claim 5, wherein said fluid is ascites fluid from patients with ovarian cancer.

9. A method to separate CEA and/or CA 19-9 from TPA comprising:

a) adding a fluid containing CEA and/or CA 19-9 and TPA to a hydrophobic interaction chromatography media in the presence of a phosphate buffer at about physiological pH; and b) collecting the eluant.

10. The method of claim 9 further comprising:

a) washing the chromatography media with said buffer wherein said buffer also contains between at least about 2-3M urea; and b) collecting the eluant.

11. A method to separate CA 19-9 from CEA as recited in claim 9 further comprising freezing the eluant.

12. A method to separate CA 19-9 from CEA as recited in claim 10 further comprising combining the eluants and freezing the eluants.

13. A method to separate TPA from CEA, CA 19-9 or CA 1 25 comprising:

a) adding a fluid containing TPA to a hydrophobic interaction media in the presence of a phosphate buffer at about physiological pH said buffer also containing between at least 2.5M urea to less than 6M urea; and b) washing the chromatography media with said buffer;

c) washing the chromatography media with at least about 6M urea; and d) collecting the eluant.

* * * * *